United States Patent [19]
Goddin, Jr.

[11] Patent Number: 4,459,142
[45] Date of Patent: Jul. 10, 1984

[54] CRYOGENIC DISTILLATIVE REMOVAL OF CO₂ FROM HIGH CO₂ CONTENT HYDROCARBON CONTAINING STREAMS

[75] Inventor: Clifton S. Goddin, Jr., Tulsa, Okla.

[73] Assignee: Standard Oil Company (Indiana), Chicago, Ill.

[21] Appl. No.: 432,217

[22] Filed: Oct. 1, 1982

[51] Int. Cl.³ .............................................. F25J 3/02
[52] U.S. Cl. ......................................... 62/17; 55/68; 55/73; 62/20
[58] Field of Search ................... 62/17, 20, 24, 28, 9, 62/11, 12, 27; 55/68, 73; 208/189, 208 R

[56] References Cited

U.S. PATENT DOCUMENTS 4,370,156  1/1983  Goddin et al. .......................... 62/17

Primary Examiner—Frank Sever

[57] ABSTRACT

Carbon dioxide is removed from a carbon dioxide containing hydrocarbon stream having a varying composition of light lean oil components in the $C_3$ through $C_{10}$ range. A light lean oil recycle stream of predetermined carbon number range is produced and utilized in the cryogenic distillative process.

16 Claims, 8 Drawing Figures

BACKGROUND

FIG.1 - BACKGROUND

CRYOGENIC DISTILLATIVE REMOVAL OF $CO_2$ FROM HIGH $CO_2$ CONTENT HYDROCARBON CONTAINING STREAMS

FIELD OF THE INVENTION

The invention relates to a process for treating gaseous streams. In one aspect the invention relates to cryogenic distillative processes for removing carbon dioxide ($CO_2$) from gaseous streams. In another aspect, the invention relates to such processes for removing $CO_2$ and/or hydrogen sulfide ($H_2S$) and/or hydrocarbons from gaseous streams.

BACKGROUND OF THE INVENTION

Production of oil and gas by $CO_2$ miscible flooding for enhanced oil recovery can result in sour and low quality gas streams to be processed. A sour natural gas is a natural gas which contains, in addition to hydrocarbon components, one or more acid gases. An acid gas, is a gas, for example, hydrogen sulfide ($H_2S$) or carbon dioxide ($CO_2$), which forms an acidic aqueous solution. Gas sweetening involves nearly complete removal of $H_2S$ and most of the $CO_2$ from sour natural gases. The sweetening is almost always required before the gas can meet sales gas specifications and before the sweet gas can be processed for production of ethane, propane, butane, and higher hydrocarbon liquid products.

In recent years higher crude oil prices have stimulated development of enhanced oil recovery techniques, such as $CO_2$ miscible flooding, which can result in production of sour gas streams having a large acid gas component. In the application of $CO_2$ miscible flooding for enhanced oil recovery, the $CO_2$ content of the produced gas increases greatly, after breakthrough, even to levels of 98 mol % or higher. It is now apparent that processes well-adapted to the processing of high carbon dioxide content gaseous streams derived from $CO_2$-miscible flood produced reservoirs are highly desirable.

Cryogenic distillative processes for removing carbon dioxide from hydrocarbon containing gaseous streams have been described. Certain of these processes can include recycle of a light lean oil stream comprising, for example, $C_3$ through $C_6$ alkanes or mixtures thereof, to a demethanizing column to prevent carbon dioxide freeze up and/or a carbon dioxide removal column, and to prevent ethane-carbon dioxide azeotrope formation or to enhance the volatility of carbon dioxide relative to hydrogen sulfide in the carbon dioxide removal column.

FIG. 1, labeled "Background," illustrates the general background of the invention in greater detail. A wellstream 11 from a sour gas reservoir is flash separated 12 into a gaseous stream 13 and a liquid stream 14. The liquid stream 14 is stabilized 16 to lower the vapor pressure of the liquid stream, thereby producing a stabilized condensate stream 17 and a vapor fraction stream 15 which is typically combined with gaseous stream 13 for gas treatment 18. Gas treatment 18 for a stream from a typical sour gas reservoir typically employs conventional amine treating to separate an acid gas stream 19 containing predominantly $H_2S$ and $CO_2$ which can be further processed in a sulfur plant 20 to produce an elemental sulfur product stream 21. Gas treatment 18 also typically produces a sweet gas stream 22 which after dehydration and recovery 23 produces a sweet residue gas stream 24, a liquefied petroleum gas (LPG) stream 25, and a natural gasoline liquids (NGL) stream 26. Dotted line 27 indicates generally the functional locus of the invention herein described in detail below.

SUMMARY OF THE INVENTION

According to the invention, a feedstream is processed in a cryogenic distillative fractionation process to produce an enriched methane stream, an enriched carbon dioxide stream, and a light oil stream having a predetermined carbon number range, at least a portion of which light oil stream is returned to one or more distillation columns of the cryogenic distillative fractionation process.

The invention is a process for cryogenic distillative fractionation comprising, from a stream containing methane, carbon dioxide, and a mixture of $C_3$ and greater hydrocarbons varying in composition, (a) removing a methane enriched overhead steam in a demethanizer column, (b) removing a carbon dioxide enriched overhead stream in a carbon dioxide removal column, (c) removing at least a light-distillate fraction and a heavy bottoms fraction to produce a light oil stream having a predetermined carbon number range, and (d) returning at least a portion of the light oil stream to an overhead of at least one of the demethanizer column and the carbon dioxide removal column as an agent for extractive distillation.

Further according to the invention is such a process where the heavy bottoms fraction is removed by a topping distillation column and the light distillate fraction is removed as an overhead stream in a stabilizer column.

Further according to the invention is such a process where the heavy bottoms fraction is removed from the stream prior to the stabilizer column.

Further according to the invention is such a process where the heavy bottoms fraction is removed from the stream subsequent to the stabilizer column.

Further according to the invention is such a process comprising introducing a feedstream containing methane, acid gas component, and a light oil component variable in composition into a topping distillation column and removing the heavy bottoms fraction from the feedstream therein to produce a topped feedstream, introducing the topped feedstream into the demethanizer column and removing methane therefrom to produce the enriched methane overhead stream and a first bottoms stream, introducing the first bottoms stream into the carbon dioxide removal column and removing carbon dioxide therefrom to produce the enriched carbon dioxide overhead stream and a second bottoms stream, and introducing the second bottoms stream into the stabilizer column and removing the light distillate fraction therefrom in an overhead stream containing the light distillate fraction, and, as a bottoms stream, the light oil stream having a predetermined carbon number range of 3 to 6.

According to another further aspect of the invention is such a process comprising introducing a feedstream comprising methane, carbon dioxide, and a light oil component variable in composition, into the demethanizer column and removing methane therefrom to produce the enriched methane overhead stream and a first bottoms stream, introducing the first bottoms stream into the carbon dioxide removal column and removing carbon dioxide therefrom to produce an enriched carbon dioxide overhead stream and a second bottoms stream, introducing the second bottoms stream into the stabilizer column and removing the light distillate fraction therefrom in an overhead stream containing the light distillate fraction and a third bottoms stream, and introducing at least a portion of the third bottoms stream into a topping distillation column to remove the heavy bottoms fraction therefrom to produce the light oil stream having a predetermined carbon number range in the range of 3 to 6.

As used herein, "light distillate fraction" means a fraction derived from the process stream introduced into the stabilizer column which contains substantially all components thereof with carbon number lower than $C_L$, plus as determined by the stabilizer column set point, a controlled fraction of $C_L$ and higher hydrocarbons; "heavy bottoms fraction" means a fraction derived from the process stream introduced into the topping column which contains substantially all components thereof heavier than $C_H$, plus as determined by the topping column set point, a controlled fraction of $C_H$ and lower hydrocarbons; and "light oil" means any of $C_3$ through $C_{10}$ alkane hydrocarbons; and "indigenous light oil" means light oil derived from the feedstream to the invented process. To produce a lean oil stream of predetermined carbon number range of 3 to 6, it is apparent that $3 \leq L \leq H$ and $4 \leq H \leq 6$.

Further aspects of the invention will be described below in the detailed description of the invention and the drawings, in which.

DESCRIPTION OF THE INVENTION

Figure 1:
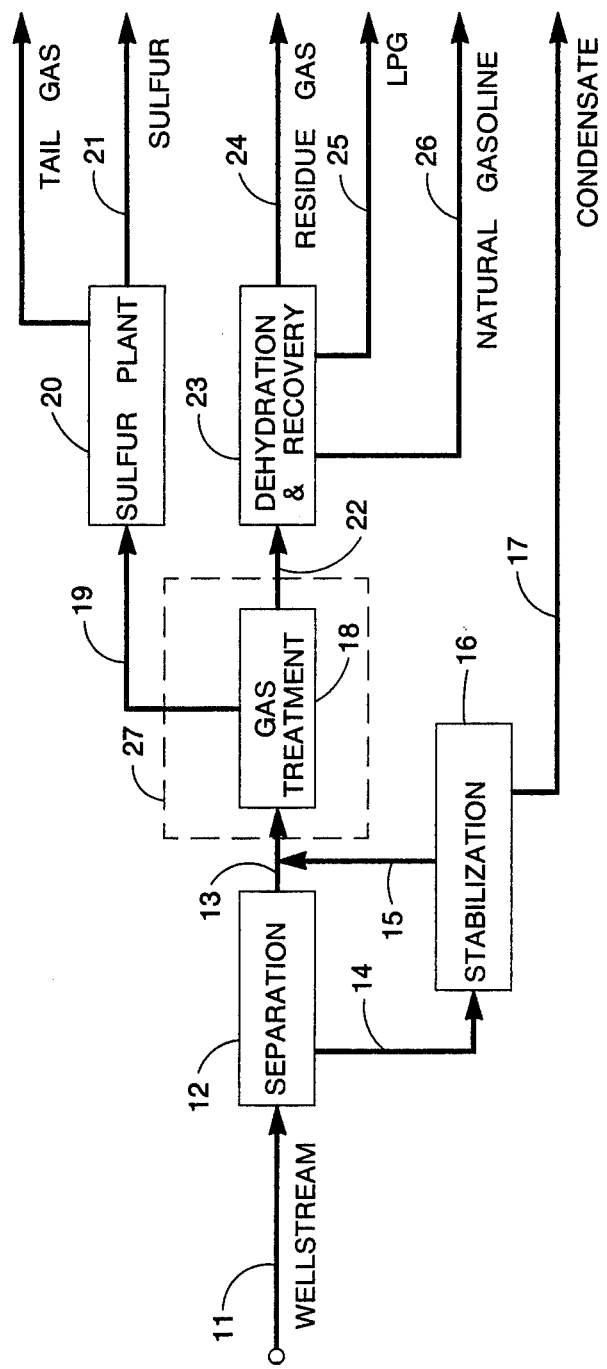
FIG. 1 represents a block diagram of a sour gas processing plant showing the background of the invention and indicating by dotted line 27 the functional site of the invention.

According to the invention, a gaseous stream comprising methane, ethane, acid gas component, and a light oil component variable in composition is processed by cryogenic distillative fractionation to produce an enriched methane stream and an enriched carbon dioxide stream. The carbon dioxide preferably comprises in the range of about 20 to about 95 mole percent (mol %) carbon dioxide and hydrocarbon sulfide can also be present. The light oil component can comprise any of $C_3$ through $C_{10}$, or even higher, alkane hydrocarbons or mixtures thereof and the light oil component is variable in composition, that is, the amounts and relative proportions of the compounds vary during processing of the stream.

According to a preferred embodiment, the gaseous stream can be from, for example, a wellhead gas separator where the well is producing from a reservoir undergoing enhanced oil recovery using carbon dioxide-miscible flooding. Such a wellhead gas separator stream during the course of production from the reservoir can show widely varying composition. In such a stream, for example, the carbon dioxide content of the wellhead gas can vary from essentially zero percent even to such as 98 mol % or higher with a rate of carbon dioxide buildup differing for each field, depending on reservoir geometry and heterogeneity, injection schedule, and other factors. In addition, the other components of the produced gas stream can also vary. Thus, for example, flash calculations indicate that the proportion of the various indigenous light lean oils, especially, but not limited to, $C_4$ and heavier hydrocarbons, can vary with varying amounts of carbon dioxide. The proportion of $C_4$ and heavier hydrocarbons, for example, can show a marked increase as the carbon dioxide level increases, for example, during the course of a flood. These aspects of the gaseous streams will be further described below in the detailed description of FIGS. 4 and 5.

According to the invented process, a light lean oil stream having a predetermined average carbon number range is produced from the above described feedstream by removing methane, carbon dioxide, light distillate fraction, and a heavy bottoms fraction in respective distillation columns. The light lean oil recycle stream preferably has an average carbon number in the 3 to 6 range between the light distillate and heavy bottoms fractions. As the average carbon number of the recycle stream increases, pumping duty, to maintain an equivalent molal circulation rate, also increases and accordingly it is currently preferred that the average carbon number be less than 6. Thus the recycle lean oil stream is preferably in the $C_3$ through $C_6$ range. More preferably, the light lean oil stream can be in the $C_4$–$C_5$ range average carbon number 4 to 5 to minimize overhead losses which can result when $C_3$ is utilized. Most preferably, the light lean oil stream can be predominantly $C_4$ (butane) to permit lower reboiler temperatures and lower volumetric lean oil circulation rates. It will also be appreciated from the following description of the invented process that in the cases where the light lean oil recycle stream comprises predominantly a single hydrocarbon species or two adjacent hydrocarbon species, for example, $C_4$ and $C_5$ hydrocarbons, then carbon number control can be in effect composition control, and such is currently preferred over the situation where more than two hydrocarbon species are utilized. Process provision can be made to monitor and maintain control of the light lean oil composition. A particular advantage of using light lean oil constituents in the $C_3$ to $C_6$ range is that with many feedstocks, a net production of natural gas liquids containing such constituents can be achieved and no external source of light lean oil constituents will be required.

The invented process can maintain the light lean oil recycle stream at a predetermined carbon number range which is independent of the average carbon number in the feedstream to the invented process. As further described herein, the hydrocarbon constituents of the feedstream can vary during processing and, in the absence of controlling the average carbon number of the light lean oil recycle stream in accordance with the invention, the operating conditions of the demethanizer column and/or the carbon dioxide removal column to which the light lean oil recycle stream can be returned can undergo wide changes and can become difficult to control.

Referring now to the drawings and in particular to FIG. 1, dotted line 27 indicates generally the functional site of the process according to the invention in a typical sour gas processing plant. Other uses of the invention can, of course, be made and it is not intended by the illustration of FIG. 1 to limit the invention thereto, but to illustrate a preferred application of the invention. Other portions of FIG. 1 have been described above relating to the BACKGROUND OF THE INVENTION and will not be repeated here.

Figure 2:
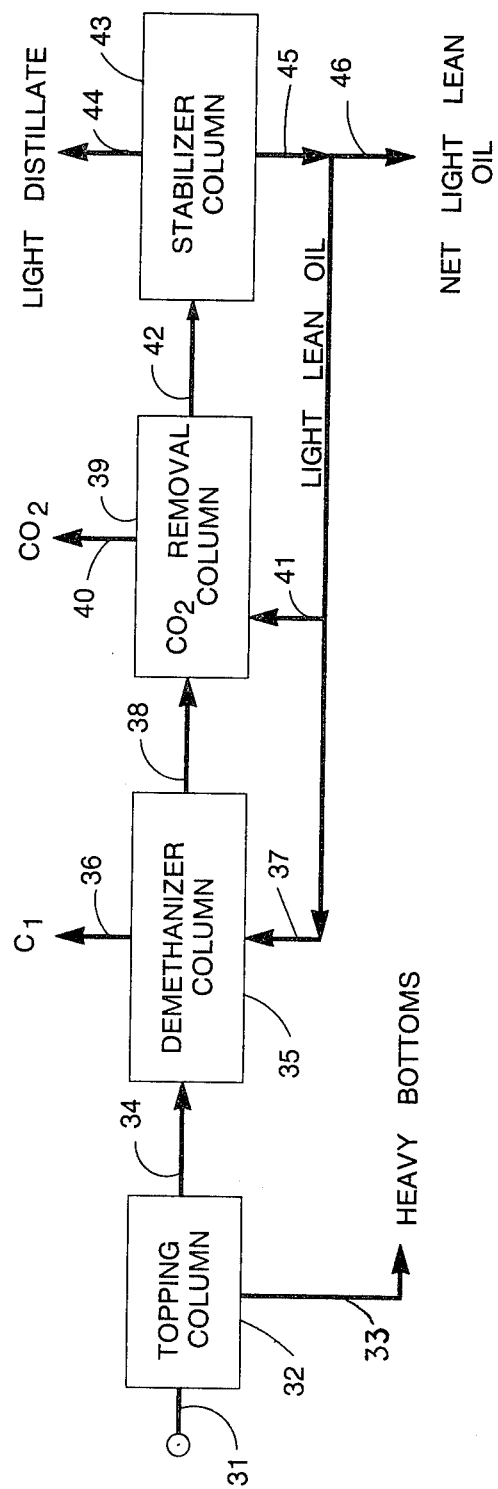
FIG. 2 represents a block diagram of one embodiment of the invention.

Referring now to FIG. 2, FIG. 2 represents a block diagram of a process according to a preferred embodiment of the invention, utilizing a topping column in the feedstream prior to the demethanizer column. Line 31 represents a gaseous stream containing methane, carbon dioxide and hydrogen sulfide, and $C_2$ through $C_7$ or higher hydrocarbons in varying amounts as constituents of the light oil component. Line 31 is introduced at an intermediate level into topping column 32 which is operated under conditions effective for separation of feedstream 31 into a bottoms stream 33 containing the predetermined heavy bottoms fraction of higher boiling point constituents of the feedstream 31, and into an overhead topped stream indicated by line 34, comprising virtually all of the $CO_2$, methane, and preferably, $C_L$ to $C_H$ hydrocarbons.

The overhead ("topped") stream 34 from the topping column is introduced into demethanizer column 35 at an intermediate level. A light lean oil recycle stream is introduced near the top of demethanizer column 35, indicated in FIG. 2 by line 37.

Demethanizer column 35 can be operated under suitable conditions and light lean oil stream 37 can be introduced into the column 35 at such a rate that column 35 is effective for producing a high purity methane overhead stream 36 and a first bottoms stream 38 containing virtually all of the carbon dioxide, hydrogen sulfide and $CO_2$, and $C_2$ and heavier hydrocarbons present in stream 34.

First bottoms stream 38 is introduced into carbon dioxide removal column 39 at an intermediate level and the light lean oil recycle stream, indicated by line 41, can be introduced near the top of column 39 to prevent ethane-carbon dioxide azeotrope formation and to increase the volatility of carbon dioxide relative to hydrogen sulfide to facilitate separation of the acid gas constituents. Column 39 can be operated under such conditions and the light lean oil recycle stream 41 can be introduced at such a rate, that column 39 is effective for producing a high purity carbon dioxide overhead stream 40 and a second bottom stream 42 containing virtually all of the hydrogen sulfide and $C_2$ and heavier hydrocarbons present in stream 38.

Second bottoms stream 42 is introduced into stabilizer column 43 at an intermediate level. Stabilizer column 43 is operated at suitable conditions to effect, preferably, separation of the light distillate fraction of hydrocarbons into an overhead stream 44 from column 43 and a predetermined portion of $C_L-C_H$ hydrocarbons into third bottoms stream 45, thereby producing the light lean oil recycle stream of predetermined average carbon number range according to the invention. Excess $C_L-C_H$ hydrocarbons consistent with maintaining a component material balance across the process can be removed by line 46.

Figure 3:
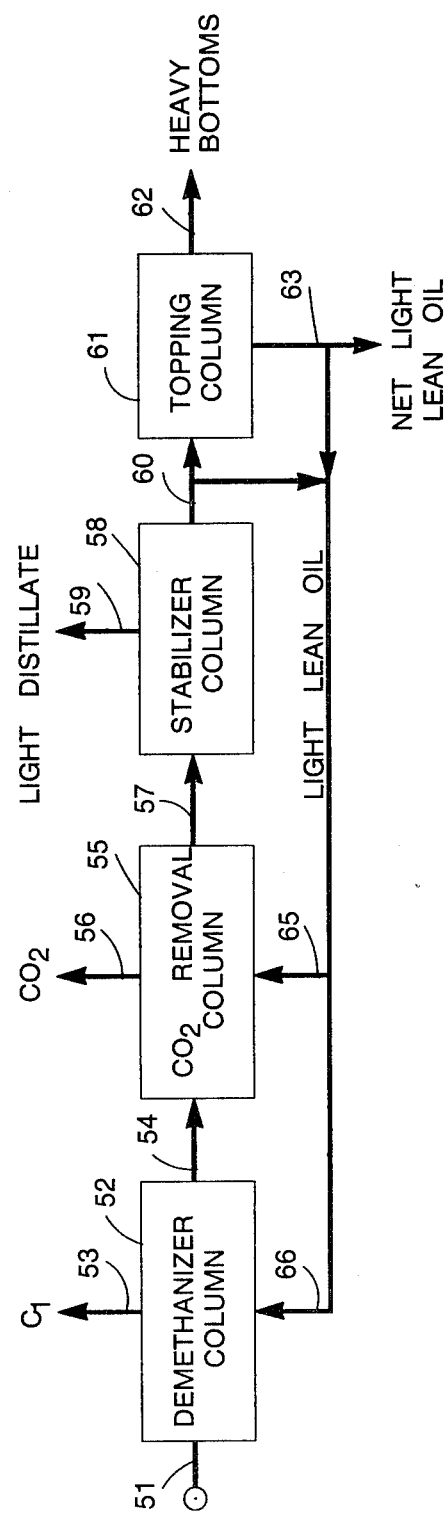
FIG. 3 represents a block diagram of a second embodiment of the invention.

Referring now to FIG. 3, FIG. 3 represents a block diagram of a process according to another preferred embodiment of the invention utilizing a topping column on the bottoms stream from the stabilizer column.

Line 51 representing a gaseous stream containing methane, $C_2$ through $C_6$ or heavier hydrocarbons, and carbon dioxide and hydrogen sulfide is introduced at an intermediate level into demethanizer column 52 which is operated to produce a sweet high purity methane overhead stream 53 and a first bottoms stream 54 containing virtually all of the carbon dioxide and hydrogen sulfide, and $C_2$ and heavier hydrocarbons. A light lean oil stream, indicated by line 66, can be introduced near the top of demethanizer column 52 in an amount effective to prevent carbon dioxide freeze-up of the column 52.

First bottoms stream 54 can be introduced at an intermediate level into carbon dioxide removal column 55 which can receive a light lean oil recycle stream 65 near the top thereof and which is operable to produce a sweet high purity $CO_2$ overhead stream 56 and a second bottoms stream 57 containing virtually all of the hydrogen sulfide and $C_2$ and heavier hydrocarbons.

Second bottoms stream 57 can be introduced at an intermediate level into stabilizer column 58 which is operated to produce an overhead stream 59 containing preferably virtually all of the light distillate fraction hydrocarbons, and to control the light end composition of the light lean oil recycle stream, and to produce a third bottoms stream 60 containing preferably a predetermined amount of $C_L$-plus hydrocarbons. A slip stream from the third bottoms stream 60 can be introduced at an intermediate level into topping column 61 which is operated to produce a fourth bottoms stream 62 containing the heavy bottoms fraction hydrocarbons, and a light lean oil recycle overhead stream 63 comprising mostly $C_L-C_H$ hydrocarbons. The heavy bottoms stream hydrocarbons can be removed by line 62.

Figure 4:
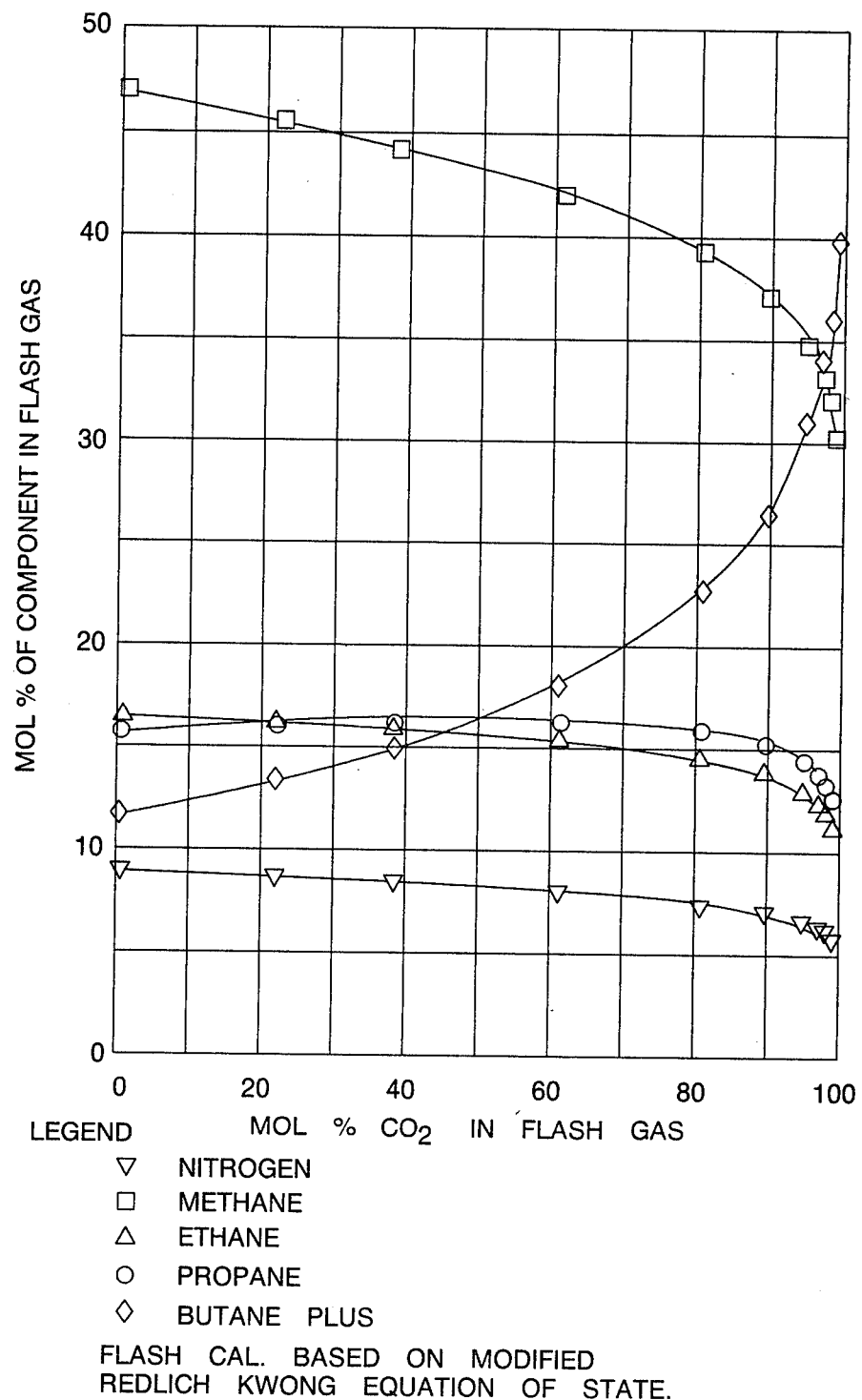
FIG. 4 represents graphically variations in the hydrocarbon fraction (on an acid gas free basis) of wellhead separator gas streams with $CO_2$ content.

Referring now to FIG. 4, FIG. 4 illustrates graphically the composition and variation in hydrocarbon content (reported on an acid gas free basis) expected in the flash gas from a field separator operating, for example, at 100° F. and 30 psia, for varying mol % $CO_2$ in the flash gas. The curves are based upon calculations based on flashing mixtures of a West Texas reservoir oil of known composition using a modified Redlich-Kwong Equation of State (see, for example, K. C. Chao and R. L. Robinson, Jr., Equations of State in Engineering and Research, Ch. 21, "Applications of a Generalized Equation of State to Petroleum Reservoir Fluids," Adv. Chem. Ser. 182, Am. Chem. Soc., Washington, D.C., (1979); and Turek, et al., Phase Equilibria in Carbon Dioxide-Multicomponent Hydrocarbon Systems: Experimental Data and an Improved Prediction Technique, Print of paper presented at 55th Annual Fall Technical Conference and Exhibition of the Society of Petroleum Engineers, Dallas, Tex., September, 1980).

FIG. 4 illustrates that, for example, as the $CO_2$ content of the well separator flash gas increases, for example, after $CO_2$ breakthrough during recovery from a $CO_2$ miscible flooding recovery project, the hydrocarbon fraction comprising $C_4$ and heavier hydrocarbons, designated "Butane Plus" in FIG. 4, increases rapidly with the increase in $CO_2$ content especially above about 60 mol % $CO_2$ in the flash gas. Conversely, the methane fraction falls off increasingly rapidly especially above about 60 mol % $CO_2$. Nitrogen, ethane, and propane functions also decline at higher $CO_2$ levels. Accordingly, the invented process becomes increasingly important for control of the light lean oil recycle stream at higher $CO_2$ levels such as above about 60 mol % $CO_2$.

Figure 5:
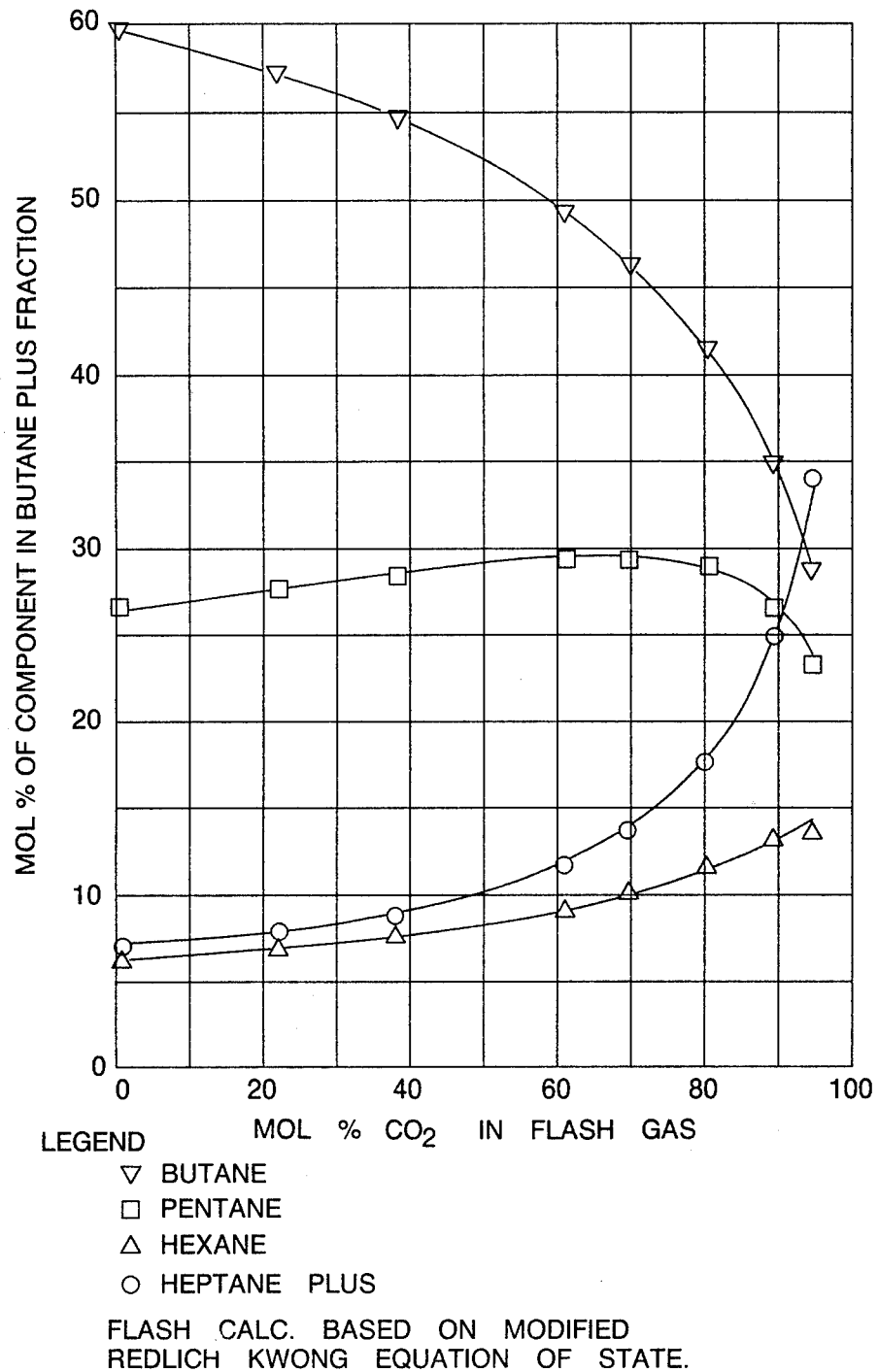
FIG. 5 represents graphically variations in composition of the Butane-Plus ($C_4$ and heavier hydrocarbons) fraction of a wellhead separator gas stream with $CO_2$ content.

FIG. 5 (based upon flash calculations using a modified Redlich Kwong Equation of State as set forth above in reference to FIG. 4) represents graphically variations in the composition of the Butane Plus fraction ($C_4$ and heavier hydrocarbons) from a wellhead separator gas stream as a function of $CO_2$ content. As indicated above for FIG. 4, the Butane Plus fraction increases rapidly at high $CO_2$ levels, for example, above about 60 mol % $CO_2$. FIG. 5 indicates that the increase in Butane-Plus fraction can involve a decrease in $C_4$ and $C_5$ hydrocarbons and an increase in $C_6$ (Hexane) and heavier ("Heptane Plus") hydrocarbons. The ratio of the hydrocarbons relative to one another can also change. As indicated above, the amounts of light and heavy hydrocarbons must therefore be adjusted during production to maintain a predetermined carbon number range in the light lean oil recycle stream. At steady state, this also involves removing hydrocarbons at the same rate as incoming. FIG. 5 indicates that in the illustrated case, the adjustment can involve removal of an increasing proportion of heavier hydrocarbons as well as in the preferred embodiment, adjustment of the relative proportions of lighter hydrocarbons.

Figure 6:
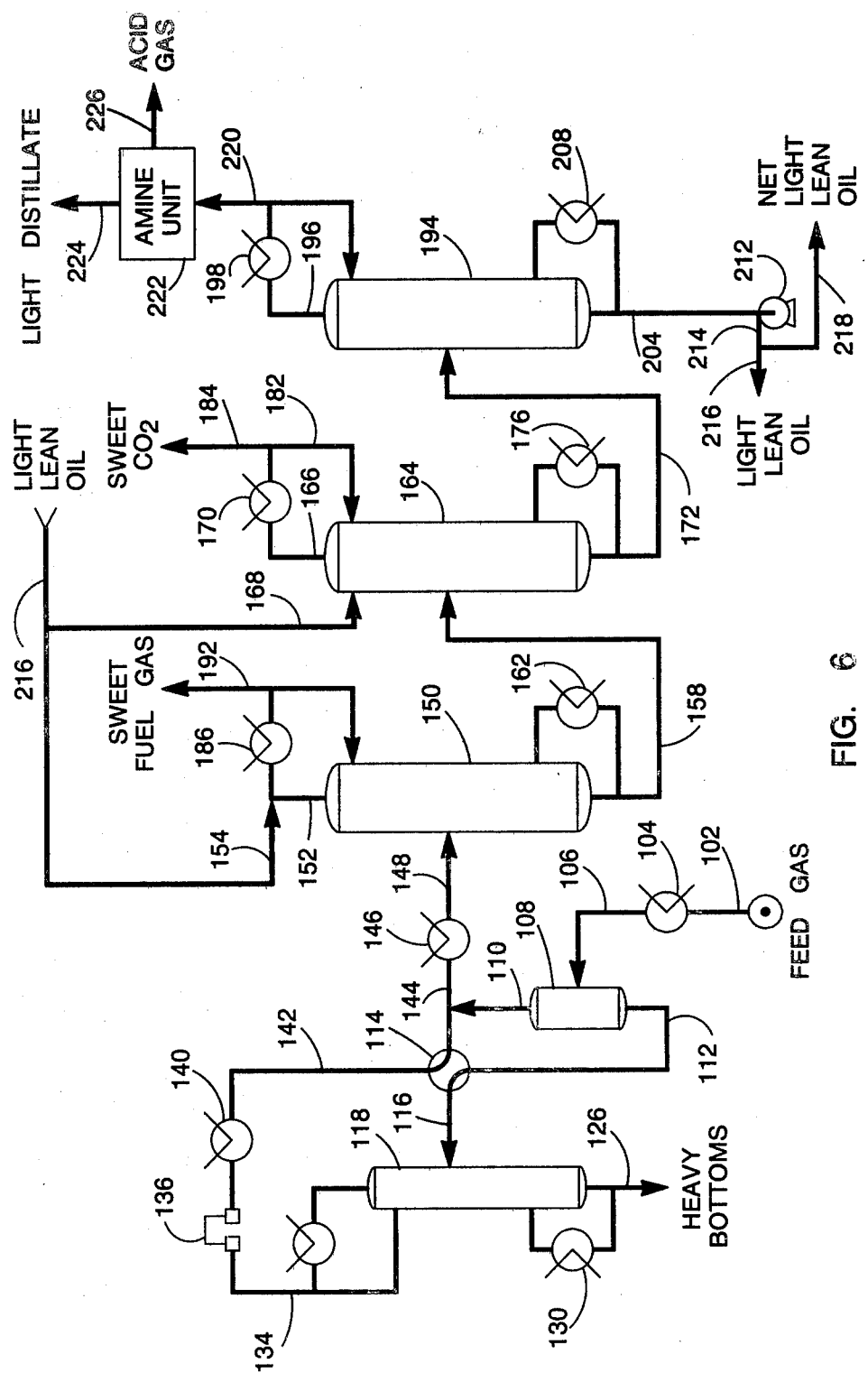
FIG. 6 represents schematically an embodiment of the invention according to FIG. 2.

FIG. 6 represents schematically a flow diagram of the preferred embodiment according to FIG. 2.

Referring now to FIG. 6 in detail, feedstream 102 having, for example, about 60 mol % carbon dioxide therein at 120° F. and 625 psia and having the following illustrative composition:

| Component | Mols/hr | Mol % |
|---|---|---|
| $N_2$ | 141 | 3.2 |
| $CO_2$ | 2686 | 60.0 |
| $H_2S$ | 8 | 0.2 |
| $C_1$ | 750 | 16.7 |
| $C_2$ | 278 | 6.2 |
| $C_3$ | 291 | 6.5 |
| $C_4$ | 159 | 3.6 |
| $C_5$ | 96 | 2.1 |
| $C_6$ | 31 | 0.7 |
| $C_7$-plus | 38 | 0.8 |
| Total | 4478 | 100.0 |

Stream 102 can be chilled in exchanger 104 to about 65° F. The chilled feedstream is introduced via line 106 into flash vessel 108 and vapor containing most of the carbon dioxide and, for example, C1 through C3 hydrocarbons can be removed by line 110 and a flash liquids stream can be removed by line 112. The flash liquids stream 112 can have the following illustrative composition:

| Component | Mols/hr |
|---|---|
| $N_2$ | 3 |
| $CO_2$ | 253 |
| $H_2S$ | 1 |
| $C_1$ | 33 |
| $C_2$ | 43 |
| $C_3$ | 99 |
| $C_4$ | 88 |
| $C_5$ | 72 |
| $C_6$ | 28 |
| $C_7$-plus | 36 |
| Total | 656 |

Thus the flash vessel 108 can be effective for removing a preponderance of the lighter components of stream 102 as a vapor fraction while leaving behind most of the heavier hydrocarbon constituents, preferably $C_6$ and heavier constituents, in the liquid fraction, thereby reducing and minimizing the volume of fluid to be processed in topping column 118. Flash liquid stream 112 is then heated in exchanger 114 in heat exchange relation with topped stream 142 as herein described to conserve refrigeration. Heated stream 116 from exchanger 114 is introduced at an intermediate level into topping column 118 which can be operated, for example, at 175 psia and having a bottom temperature of 384° F. and an overhead temperature of 132° F. Column 118 can be operated to remove a heavy bottoms stream 126 containing preferably virtually all of the $C_6$ and heavier hydrocarbons and having, for example, the following exemplary composition:

| Component | Mols/hr |
|---|---|
| $C_5$ | 5 |
| $C_6$ | 26 |
| $C_7$-plus | 36 |
| Total | 67 |

The topping column net overhead vapor stream 134 can be recompressed 136 and cooled in exchanger 140 to produce cooled topped stream 142 at about 120° F. and 625 psia having the following illustrative composition:

| Component | Mols/hr |
|---|---|
| $N_2$ | 3 |
| $CO_2$ | 253 |
| $H_2S$ | 1 |
| $C_1$ | 33 |
| $C_2$ | 43 |
| $C_3$ | 99 |
| $C_4$ | 88 |
| $C_5$ | 67 |
| $C_6$ | 2 |
| Total | 589 |

Cooled topped stream 142 can be cooled in heat exchanger 114 in indirect heat exchange relation with flash liquid stream 112 and combined with flash vapor stream 110 to produce combined stream 144 at about 77° F. and 620 psia, having the following illustrative composition:

| Component | Mols/hr |
|---|---|
| $N_2$ | 141 |
| $CO_2$ | 2686 |
| $H_2S$ | 8 |
| $C_1$ | 750 |
| $C_2$ | 278 |
| $C_3$ | 291 |
| $C_4$ | 159 |
| $C_5$ | 91 |
| $C_6$ | 5 |
| $C_7$-plus | 2 |
| Total | 4411 |

Comparison of the illustrative compositions of streams 102 and 144 illustrates, for example, that virtually all $C_6$ and heavier hydrocarbons can be removed from the process stream via topping column heavy bottoms stream 126.

Combined stream 144 can be cooled in exchanger 146 to, for example, about −20° F. to produce the demethanizer column feedstream 148 which can be introduced into demethanizer column 150 at an intermediate level. Demethanizer column 150 is operated under conditions to effect separation of methane in a overhead stream as described in more detail below. A light lean oil recycle stream 154 derived as herein described can be introduced into the overhead vapor line 152 from column 150. The condenser outlet can be maintained at about −80° F. and the column bottom can be maintained at about 60° F. The light lean oil stream 154 can be introduced at a rate effective to prevent freeze up of $CO_2$ in the condenser and demethanizer column 150 while the demethanizer column 150 can be operated to produce a specification methane overhead stream and to remove most of the carbon dioxide and hydrogen sulfide in the bottoms stream 158.

Overhead stream 152 can be cooled in refrigerated overhead condenser 186 and the condensate plus lean oil returned to the top of demethanizer column 150. The enriched methane vapor product can be removed by line 192. Reboiler 162 can be used to maintain the bottom of column 150 at the desired temperature, for example, 60° F. The product methane stream 192 can have the following illustrative composition:

| Component | Mols/hr | Mol % |
|---|---|---|
| $N_2$ | 141 | 15.8 |
| $CO_2$ | 13 | 1.5 |
| $C_1$ | 735 | 82.4 |
| $C_4$ | 2 | 0.2 |
| $C_5$ | 1 | 0.1 |
| Total | 892 | 100.0 |

Bottoms stream 158 comprising the acid gas component and virtually all of the $C_2$ and higher hydrocarbons which were present in stream 148 can be introduced at an intermediate level into carbon dioxide column 164 operated at about 450 psia. A light lean oil recycle stream 168 can be introduced near the top of the $CO_2$ removal column 164 at a rate effective to prevent ethane-$CO_2$ azeotrope formation and to increase the volatility of carbon dioxide relative to hydrogen sulfide. The bottom of $CO_2$ removal column 164 can be maintained at about 285° F. by reboiler 176. The overhead stream 166 from the $CO_2$ removal column 164 can be cooled in refrigerated condenser 170 to provide reflux at 22° F. which can be returned via line 182 to near the top of the $CO_2$ removal column 164, while a sweet high purity carbon dioxide product stream 184 can be removed. The bottoms stream 172 from the $CO_2$ removal column can contain virtually all of the hydrogen sulfide and the $C_2$ and heavier hydrocarbons which were present in stream 158. The stream 184 can have the following illustrative composition:

| Component | Mols/hr |
|---|---|
| $CO_2$ | 2663 |
| $C_1$ | 15 |
| $C_2$ | 37 |
| $C_3$ | 1 |
| $C_4$ | 5 |
| $C_5$ | 1 |
| Total | 2722 |

Bottoms stream 172 can be introduced at an intermediate level into stabilizer column 194 operated at about 300 psia. The stabiizer column can have a bottom temperature of about 285° F. maintained by reboiler 208. The stabilizer column overhead vapor 196 can be sent to condenser 198 and the condensate at 103° F. can be returned to the column. The light distillate stream overhead 220 can be a $C_2$-$C_3$ mixture stream which is treated in amine unit 222 to produce a sweet $C_2$-$C_3$ mix 224 and an acid gas stream 226. Illustrative compositions for streams 224 and 226 can be as follows:

| Component | Stream 224 Mols/hr | Stream 226 Mols/hr |
|---|---|---|
| $CO_2$ | — | 10 |
| $H_2S$ | — | 8 |
| $C_2$ | 241 | — |
| $C_3$ | 289 | — |
| $C_4$ | 30 | — |
| Total | 560 | 18 |

The essentially propane free bottoms stream 204 of predetermined composition (and average carbon number) from stabilizer column 194 can be returned in part as the light lean oil recycle streams 154 and 168 via pump 212 and line 214 and 216 as indicated. Excess light lean oil can be removed via line 218 for further processing. An illustrative composition for stream 218 can be as follows:

| Component | Mols/hr | Mol % |
|---|---|---|
| $C_3$ | 1 | 0.5 |
| $C_4$ | 122 | 55.7 |
| $C_5$ | 89 | 40.6 |
| $C_6$ | 5 | 2.3 |
| $C_7$-plus | 2 | 0.9 |
| Total | 219 | 100.0 |

In this illustrated embodiment the lean oil composition is controlled to consist essentially of butane and pentane although small amounts of other hydrocarbons can be present.

Figure 7:
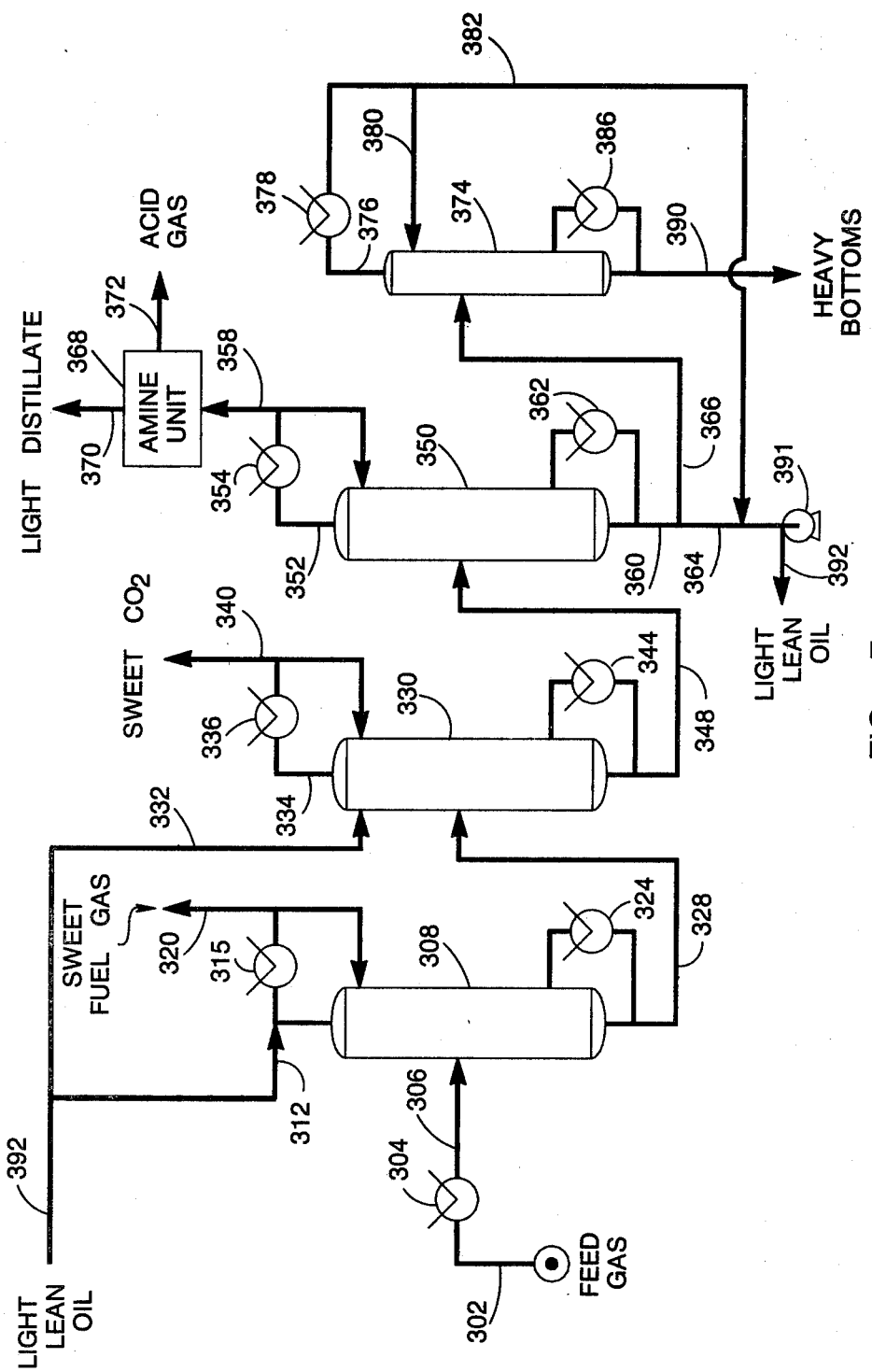
FIG. 7 represents schematically an embodiment of the invention according to FIG. 3.

Referring now to FIG. 7, FIG. 7 represents schematically a flow diagram of the preferred embodiment of FIG. 3.

The feedstream 302 comprising, for example, about 60 mol % carbon dioxide can have the same exemplary composition as given above for stream 102. The feedstream 302 can be cooled in exchanger 304 to about −20° F. in stream 306 prior to entering demethanizer column 308 which can be operated at about 600 psia. A light lean oil recycle stream can be introduced by line 312 into the overhead condenser 315 to prevent carbon dioxide freeze up during operation of the column. The bottom of demethanizer column 308 can be maintained at about 60° F. by reboiler 324. The column 308 overhead can be cooled in refrigerated condenser 315, with the condensate admixed with lean oil being returned to the top of demethanizer column 308, thereby producing a sweet specification methane overhead stream 320. Methane overhead stream 320 can have the same illustrative composition as given for stream 192.

The bottoms stream 328 containing virtually all of the $CO_2$, $H_2S$, and $C_2$ and heavier hydrocarbons present in stream 306 can be introduced at an intermediate level into carbon dioxide removal column 330, which can be operated about 450 psia. A light lean oil recycle stream 332 can be introduced near the top of the carbon dioxide removal column 330. The bottom temperature of carbon dioxide removal column 330 can be maintained by side reboiler 344. Overhead vapor 334 from column 330 can be cooled in partial condenser 336 and condensate returned to produce a high purity sweet carbon dioxide stream 340 having the same illustrative composition as given for stream 184. The bottoms stream 348 containing virtually all of the hydrogen sulfide and $C_2$ and heavier hydrocarbons can be provided as an inlet stream to the depropanizer column 350 at an intermediate level.

Stabilizer column 350 can be operated at, for example, about 300 psia with the bottom temperature being maintained by side reboiler 362. The top of the stabilizer column can be maintained at about 103° F. and the overhead vapor 352 can be cooled in exchanger 354 and condensate returned by line 356 to produce an overhead stream 358, in the preferred embodiment, consisting predominantly of $C_2$ and $C_3$ hydrocarbons and a predetermined fraction of $C_4$ hydrocarbons. The butane rejection of column 350 is controlled in conjunction with the $C_4$ rejection in the topping column bottoms to maintain composition, i.e., average carbon number of the light lean oil recycle stream. The stream 358 can be treated in an amine unit 368 of conventional design to produce a sweet $C_2$-$C_3$ mix stream 370 and an acid gas 372 stream which can be provided, for example, to a sulfur recovery unit (not shown). Streams 370 and 372 can have the following illustrative compositions:

| Component | Stream 370 Mols/hr | Stream 372 Mols/hr |
|---|---|---|
| $CO_2$ | — | 10 |
| $H_2S$ | — | 8 |
| $C_2$ | 241 | — |
| $C_3$ | 290 | — |
| $C_4$ | 30 | — |
| Total | 561 | 18 |

The composition of bottoms stream 360 from stabilizer column 350 is adjusted to constitute the light lean oil stream 392 which can be recycled to columns 308 and 330. It is important that the composition of the lean oil be controlled within relatively narrow limits. To accomplish this, a portion of the stabilizer column bottoms stream can be sent to the topping column 374, wherein rejection of $C_5$ and heavier hydrocarbons can be accomplished. The composition of the stream 366 to the topping column 374 is illustrated below. In this instance the stream 366 represents about 30% of the stabilizer bottoms stream 360.

| Component | Mols/hr | Mol. % |
|---|---|---|
| $C_3$ | 4 | 0.4 |
| $C_4$ | 815 | 78.1 |
| $C_5$ | 156 | 14.9 |
| $C_6$ | 31 | 3.0 |
| $C_7$-plus | 38 | 3.6 |
| Total | 1044 | 100.0 |

The bottoms stream 366 can be introduced at an intermediate level into topping column 374 which can be operated at, for example, about 250 psia. The bottom of topping column 374 can be maintained at about 286° F. by reboiler 386 and the top maintained at about 227° F. The overhead vapor 376 from the topping column 374, consisting of predominantly $C_4$-$C_5$ constituents of the light lean oil can be cooled in condenser 378 and the condensate returned to column 374 by line 380 and also returned by line 382 to mix with the remaining portion of stabilizer bottoms 364 to produce a light lean oil recycle stream of predetermined composition 392. The light lean oil recycle stream can be returned by pump 391 and lines 392, 312 and 332 to the demethanizer column 308 and the carbon dioxide column 330 as indicated. The topping column heavy bottoms stream 390 can have the following illustrative composition:

| Component | Mols/hr |
|---|---|
| $C_4$ | 122 |
| $C_5$ | 94 |
| $C_6$ | 31 |
| $C_7$-plus | 38 |
| Total | 285 |

The heavy bottom stream 390 from topping column 374 represents a net production of $C_4$ and heavier hydrocarbons and is removed for further processing.

Streams 382 and 392 can have illustrative compositions as follows:

| Component | Stream 382 Mols/hr | Stream 392 Mols/hr |
|---|---|---|
| $C_3$ | 4 | 14 |
| $C_4$ | 693 | 2645 |
| $C_5$ | 62 | 434 |
| $C_6$ | — | 76 |
| $C_7$ | — | 91 |
| Total | 759 | 3260 |

Either (1) the embodiment of FIGS. 2 and 6 wherein heavy hydrocarbon components are removed by topping liquid condensed by chilling the plant feed, or (2) the embodiment of FIGS. 3 and 7 wherein the heavy hydrocarbon components are removed by topping a slipstream from the lean oil recycle, can be employed to maintain the average carbon number of the light lean recycle oil within prescribed limits. Selection of the most advantageous alternate can depend to a large degree on energy costs for a particular plant location.

For comparable feedstreams as illustrated herein in reference to FIGS. 6 and 7, the following will be readily appreciated by those skilled in the art: (1) the embodiment of FIGS. 2 and 6 can utilize smaller topping columns than utilized in the embodiment of FIGS. 3 and 7; however, (2) additional refrigeration can be required by the embodiment of FIGS. 2 and 6 over what may be required by the embodiment of FIGS. 3 and 7.

It will further be appreciated that the invention described herein will be useful in processing streams containing methane, acid gas component, and a light oils component variable in composition, especially, for example, gaseous streams derived from $CO_2$ miscible flood produced reservoirs. The invented process is especially useful where a light lean oil recycle stream of about constant composition is utilized in cryogenic distillative processes for the removal of methane and/or carbon dioxide from gaseous streams.

Figure 8:
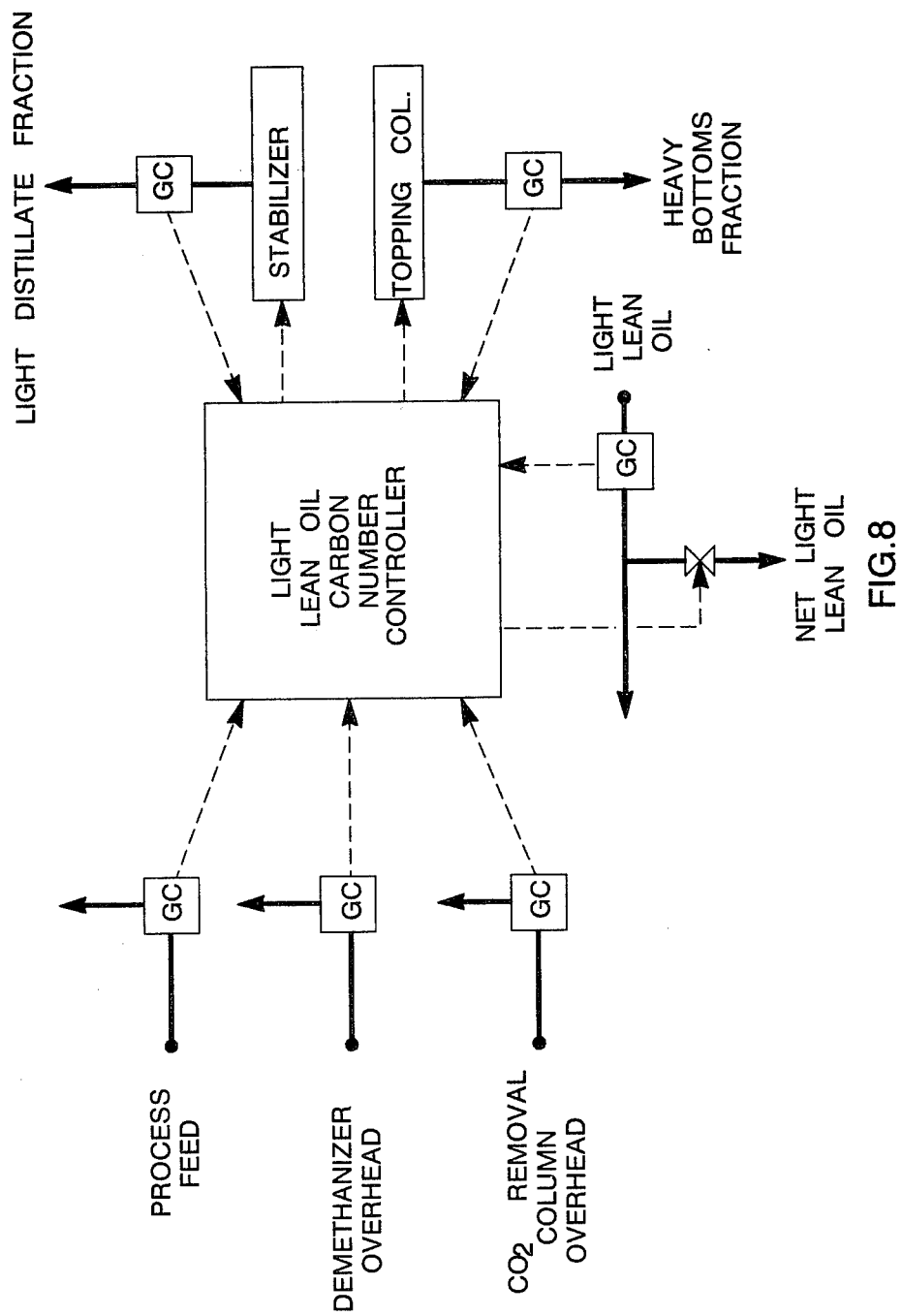
FIG. 8 represents a simplified block diagram of a control system suitable for use in the invented process.

An illustrative simplified control system is illustrated in FIG. 8. The compositions determined, for example, by gas chromatography (indicated by "GC"), along with metered flow rates, of the Light Distillate Fraction (overhead from the stabilizer column), of the Heavy Bottoms Fraction bottoms from the topping column, of the light lean oil recycle stream, and optionally of the demethanizer column overhead and of the carbon dioxide removal column overhead streams, can be provided to a carbon number controller which controls operation at least of the topping column and the stabilizer column to maintain the average carbon number of the light lean oil stream within preset limits.

While the invention has been described in terms of preferred embodiments and illustrative operating conditions and compositions given as required to illustrate the practice of the invention, many other embodiments and operating conditions and compositions will be apparent to those skilled in the art to which the invention pertains. Accordingly, the invention is not to be considered limited by the exemplary description provided herein, but by the scope of the claims appended hereto.

What is claimed is:

1. Process for cryogenic distillative fractionation of a feedstream containing methane, ethane, carbon dioxide, and a mixture of $C_3$ and greater hydrocarbons varying in composition, comprising:

maintaining a predetermined carbon number range in a light oil stream while the hydrocarbon composition of the feedstream varies by (a) removing a methane enriched overhead stream in a demethanizer column;
   (b) removing a carbon dioxide enriched overhead stream in a carbon dioxide removal column;
   (c) removing a light distillate fraction in a stabilizer column and a heavy bottoms fraction in a topping distillation column and producing the light oil stream having the predetermined carbon number range; and returning at least a portion of the light oil stream to an overhead of at least one of the demethanizer column and the carbon dioxide removal column as an agent for extractive distillation.

2. Process as in claim 1 wherein the heavy bottoms fraction is removed from the stream prior to the stabilizer column.

3. Process as in claim 1 wherein the heavy bottoms fraction is removed from the stream subsequent to the stabilizer column.

4. Process as in claim 1 comprising:
   (a) introducing a feedstream containing methane, acid gas component, and a light oil component variable in composition into a topping distillation column and removing the heavy bottoms fraction from the feedstream therein to produce a topped feedstream;
   (b) introducing the topped feedstream into the demethanizer column and removing methane therefrom to produce the enriched methane overhead stream and a first bottoms stream;
   (c) introducing the first bottoms stream into the carbon dioxide removal column and removing carbon dioxide therefrom to produce the enriched carbon dioxide overhead stream and a second bottoms stream; and
   (d) introducing the second bottoms stream into the stabilizer column and removing the light distillate fraction therefrom to produce an overhead stream containing the light distillate fraction, and, as a bottoms stream, the light oil stream having a predetermined carbon number range in the range of 3 to 6.

5. Process as in claim 1 comprising:
   (a) introducing a feedstream comprising methane, ethane, carbon dioxide, and a light oil component variable in composition, into the demethanizer column and removing methane therefrom to produce the enriched methane overhead stream and a first bottoms stream;
   (b) introducing the first bottoms stream into the carbon dioxide removal column and removing carbon dioxide therefrom to produce an enriched carbon dioxide overhead stream and a second bottoms stream;
   (c) introducing the second bottoms stream into the stabilizer column and removing the light distillate fraction therefrom to produce an overhead stream light distillate containing the fraction and a third bottoms stream, and
   (d) introducing at least a portion of the third bottoms stream into a topping distillation column and removing the heavy bottoms fraction therefrom to produce the light oil stream having a predetermined carbon number range in the range of 3 to 6.

6. Process for cryogenic distillative fractionation of a feedstream comprising methane, carbon dioxide, and an indigenous light oil component variable in composition, the process comprising:

maintaining a predetermined carbon number range in a light lean oil stream while the hydrocarbon content of the feedstream varies by removing a first hydrocarbon fraction containing lower boiling point constituents in a stabilizer column and a second hydrocarbon fraction containing higher boiling point constituents in a topping distillation column from the feedstream to produce a light lean oil stream of predetermined average carbon number range by the steps of (a) introducing a feedstream comprising methane, carbon dioxide, and an indigenous light lean oil component variable in composition into the topping column and removing the second hydrocarbon fraction containing higher boiling point constituents from the feedstream therein to produce a topped feedstream;
   (b) introducing the topped feedstream into a first distillation column and removing methane therefrom to produce an enriched methane overhead stream and a first bottoms stream;
   (c) introducing the first bottoms stream into a second distillation column and removing carbon dioxide therefrom to produce an enriched carbon dioxide overhead stream and a second bottoms stream;
   (d) introducing the second bottoms stream into the stabilizer column and removing the first hydrocarbon fraction of lower boiling point constituents therefrom to produce an overhead stream enriched in the lower boiling point constituents and, as a bottoms stream, the light lean oil stream of predetermined average carbon number range; and returning at least a portion of the light lean oil stream of predetermined carbon number range to at least one of the first distillation column and the second distillation column.

7. Process as in claim 6 further comprising:
   (a) flashing the feedstream to produce a liquid fraction containing about all the second hydrocarbon fraction; and
   (b) introducing the liquid fraction into the topping column.

8. Process as in claim 6 further comprising:
   (a) chilling the feedstream to produce a chilled feedstream;

(b) flashing the chilled feedstream to produce a vapor fraction and a liquid fraction containing about all the second hydrocarbon fraction;

(c) heating the liquid fraction in indirect heat exchange relationship with the topped input stream to produce a heated input stream for the topping column and a cooled topped feedstream; and (d) introducing the heated input stream into the topping column.

9. Process as in claim 6 wherein the light lean oil stream of predetermined carbon number range comprises $C_3$ to $C_6$ alkane hydrocarbons and mixtures thereof.

10. Process as in claim 6 wherein the light lean oil stream of predetermined composition comprises $C_4$ to $C_5$ alkane hydrocarbons.

11. Process as in claim 6 wherein the light lean oil stream of predetermined carbon number range comprises $C_4$ alkane hydrocarbons.

12. Process for cryogenic distillative fractionation of a feedstream comprising methane, carbon dioxide, and an indigenous light oil component variable in composition, the process comprising:

maintaining a predetermined carbon number range in a light lean oil stream while the hydrocarbon content of the feedstream varies by removing a first hydrocarbon fraction containing lower boiling point constituents in a stabilizer column and a second hydrocarbon fraction containing higher boiling point constituents in a topping distillation column from the feedstream to produce a light lean oil stream of predetermined carbon number range by the steps of (a) introducing a feedstream comprising methane, carbon dioxide, and an indigenous light lean oil component variable in composition, into a distillation column and removing methane therefrom to produce an enriched methane overhead stream and a bottoms stream;

(b) introducing the first bottoms stream into a second distillation column and removing carbon dioxide therefrom to produce an enriched carbon dioxide overhead stream and a second bottoms stream;

(c) introducing the second bottoms stream into the stabilizer column and removing the first hydrocarbon fraction containing lower boiling point constituents therefrom to produce an overhead stream enriched in the lower boiling point constituents and a third bottoms stream;

(d) introducing a portion of the third bottoms stream into the topping distillation column to remove the second hydrocarbon fraction containing higher boiling point constituents from the third bottoms stream to produce the light lean oil stream of predetermined carbon number range; and returning at least a portion of the light lean oil stream of predetermined carbon number range to at least one of the first distillation column and the second distillation column.

13. Process as in claim 12 wherein the light lean oil stream of predetermined carbon number range comprises $C_3$ to $C_6$ alkane hydrocarbons and mixtures thereof.

14. Process as in claim 12 wherein the light lean oil stream of predetermined carbon number range comprises $C_4$ and $C_5$ alkane hydrocarbons.

15. Process as in claim 12 wherein the light lean oil stream of predetermined carbon number comprises $C_4$ alkane hydrocarbons.

16. Process as in either of claims 6 or 12 wherein the feedstream is a wellhead gas stream from a reservoir undergoing $CO_2$ miscible flooding.

* * * * *

UNITED STATES PATENT OFFICE
CERTIFICATE OF CORRECTION

PATENT NO. : 4,459,142
DATED : July 10, 1984
INVENTOR(S) : Clifton S. Goddin, Jr., It is certified that error appears in the above-identified patent and that said Letters Patent are hereby corrected as shown below:

Column 15, Claim 12, Line 37, after "a" and Before "distil-" insert --first--.

Signed and Sealed this

Twenty-sixth Day of March 1985

[SEAL]

Attest:

DONALD J. QUIGG

Attesting Officer     Acting Commissioner of Patents and Trademarks